United States Patent [19]

House

[11] 4,324,681
[45] Apr. 13, 1982

[54] CHIRAL SUPPORTS FOR RESOLUTION OF RACEMATES

[75] Inventor: David W. House, Arlington Heights, Ill.

[73] Assignee: UOP Inc., Des Plaines, Ill.

[21] Appl. No.: 158,750

[22] Filed: Jun. 12, 1980

[51] Int. Cl.$^3$ ............................................. B01D 15/08
[52] U.S. Cl. ................................... 252/184; 210/635; 210/656; 210/659; 252/430; 252/455 R; 252/463; 428/407; 428/702
[58] Field of Search .................. 252/184, 430, 455 R, 252/463; 210/635, 656, 659; 428/404, 407, 451, 702

[56] References Cited

U.S. PATENT DOCUMENTS 4,111,838  9/1970  Schaeffer ........................ 210/656
4,159,966  7/1979  Roberts .......................... 252/430

OTHER PUBLICATIONS

Henderson et al., Nature, vol. 141 (May 21, 1938), pp. 917-918; vol. 142 (Jul. 23, 1938), pp. 162-163.
Blaschke et al., Chemische Berichte vol. 109 (1976) pp. 1967-1975.
Baczuk et al., J. of Chromatography, vol. 60 (1971) pp. 351-361.

*Primary Examiner*—Benjamin R. Padgett
*Assistant Examiner*—Irwin Gluck
*Attorney, Agent, or Firm*—James R. Hoatson, Jr.; Eugene I. Snyder; William H. Page, II

[57] ABSTRACT

A silylated silica or alumina covalently bonded to a chiral amino acid through a carboxyl group of said acid may be used as the solid stationary phase in the chromatographic resolution of racemic mixtures. Several classes of derivatives of such bound chiral amino acids also may be used in the resolution of racemates. Such derivatives include N-alkyl and N-acyl derivatives, and esters where the amino acid is a dicarboxylic acid or contains a hydroxy group.

9 Claims, No Drawings

CHIRAL SUPPORTS FOR RESOLUTION OF RACEMATES

BACKGROUND OF THE INVENTION

Ever since Pasteur discovered the property of optical activity displayed by chiral compounds, the resolution of racemic mixtures into their enantiomeric components has posed a challenge. Substantial progress in separating enantiomeric pairs has been achieved since Pasteur's laborious hand separation of the enantiomeric crystals of racemic sodium ammonium tartrate, yet methods of resolution, and the materials used therefor, remain a formidable obstacle to commercial production of optically active organic substances.

A traditional method of resolution comprises reacting a racemic mixture with a second optically active substance to form a pair of diastereomeric derivatives. Such derivatives generally have different physical properties which permit their separation by conventional means. For example, fractional crystallization often permits substantial separation to afford at least one of the diastereomers in a pure state, or largely so. An appropriate chemical transformation then converts the purified derivative, which was formed initially solely to prepare a diastereomeric pair, into one enantiomer of the originally racemic compound. This traditional method is exemplified by the reaction of naturally occurring optically active alkaloids, for example, brucine, with racemic acids to form diastereomeric salts, with release of an optically active organic acid from a purified diastereomer upon acidification of the latter.

Such traditional methods suffer from many limitations. Generally, only one of the enantiomeric pairs can be obtained, so yields are necessarily less than 50%. The separation of the material so obtained usually is incomplete, leading to materials with enhanced rather than complete optical purity. The optically active materials used to form the diastereomers frequently are expensive and quite toxic—the alkaloids as a class are good examples—and are only partially recoverable. Regeneration of optically active material from its derivative may itself cause racemization of the desired compound, leading to diminution of optical purity. For example, if optically active benzyl alcohols are prepared through their diastereomeric ester derivatives, subsequent acid hydrolysis of the latter to regenerate the alcohol may be accompanied by appreciable racemizaton.

With the advent of chromatography diverse variations on the basic method of separating diastereomers became possible. These approaches undeniably represent substantial advances in the art, yet fail to surmount the basic need, and associated problems, to prepare diastereomeric derivatives of the desired compound and to transform such derivatives after separation to the optically active compounds of interest.

Chromatographic methods of separation offer the advantages of general application, mild conditions which generally preclude chemical or physical transformation, efficiency of recovery and separation which are limited only by the number of theoretical plates employed, and the capability of utilization from a milligram to kilogram scale. Translation from a laboratory to industrial scale has proved feasible, and commercial processes employing chromatographic separation occupy an important position in the arsenal of available industrial methods. For such reasons, methods based on chromatographic separation remain under intensive exploration.

To circumvent the disadvantage of separating diastereomeric derivatives of a compound while retaining the advantages of chromatographic separation, recent advances in the art have employed chiral, optically active compounds in association with the chromatographic support. The theory underlying this approach is that chiral material will have differential weak interactions with enantiomers, for example, hydrogen bonding, or acid-base interactions generally. Such weak interactions lead to reversible formation of entities which we refer to as complexes, and the equilibrium constant characterizing complex formation will differ for each member of the enantiomeric pair. The different equilibrium constants manifest themselves as a differing partition coefficient among the phases in a chromatographic process, leading ultimately to separation of enantiomers.

Thus, enantiomers of some chromium complexes were resolved by chromatography on powdered quartz, a naturally occurring chiral material. Karagounis and Coumolos, *Nature*, 142, 162(1938). Lactose, another naturally occurring chiral material, was used to separate p-phenylene-bis-iminocamphor. Henderson and Rule, *Nature*, 141, 917(1938). However, despite this knowledge substantiating theoretical considerations, advances in the art have been tortuous at best.

A major obstacle has been development of a chiral solid phase capable of resolving, at least in principle, a broad class of racemic organic compounds, with a stability which permits repeated usage, and with adequate capacity to make separation feasible on a preparative scale. Gil-Av has made a major contribution toward one kind of solution by gas-liquid phase chromatographic resolution of enantiomers using columns coated with N-trifluoroacetyl derivatives of amino acids, di- and tri-peptides. Gil-Av and Nurok, "Advances in Chromatography", Volume 10, Marcel Dekker (New York), 1974. However, the advances suffer practical limitations originating from the need to have volatile substrates and the inability to scale up methods employed.

Another advance is represented by the work of Baczuk and coworkers, *J. Chromatogr.*, 60, 351(1971), who covalently bonded an optically active amino acid through a cyanuric acid linkage to a modified dextran support and utilized the resulting material in column chromatography to resolve 3,4-dihydroxyphenylalanine. A different approach is exemplified by polymerization of optically active amides with the resulting polymer used as a solid phase in liquid-solid chromatography. Blaschke and Schwanghart, *Chemische Berichte*, 109, 1967(1976).

General considerations of the characteristics of a solid phase chiral chromatographic medium, including such factors as structural integrity, flow characteristics, chemical inertness, reusability, capacity, and incorporation into well developed commercial processes, suggest that a desirable material will be comprised of (1) a solid, largely inorganic support, bearing a (2) pendant functional group sufficiently removed from the surface of the support so that it may (3) covalently bond with a suitable site of a chiral molecule while enabling the latter to at least simulate its homogeneous interactions with racemic compounds it encounters.

SUMMARY

An object of this invention is to provide chiral material which can be used as a solid stationary phase in the chromatographic separation of racemic mixtures. An embodiment of this invention comprises a silylated inorganic oxide covalently bonded to a chiral amino acid via a formed amide linkage. In a more specific embodiment the silicon containing portion is a 3-propylsilyl group. In another more specific embodiment the amino acid is a naturally occurring amino acid.

DESCRIPTION OF THE INVENTION

A consideration of the theoretical mode of separation of racemates by chiral solid phase chromatographic media and desirable functional attributes of such media has led to compositions described herein. Said compositions of this invention are comprised of three parts: 1. an inert core support, providing mechanical strength, good flow properties, and being capable of chemically binding with a spacer molecule, with or without prior modification of the surface of the core support; 2. a spacer molecule, which is a chemical grouping one end of which is chemically bonded to the core support, the other end of which initially bears a functional group maintained at some distance from the surface of the core support by mediating atoms or groups of atoms; and 3. chiral material covalently bonded to the remaining terminus of the spacer molecule via the aforementioned functional group so as to retain its chirality (i.e., bonding does not destroy chirality) and to preserve substantially the physical and chemical properties exhibited in homogeneous media.

The core supports of this invention include metal oxides, glass, and ceramic materials. Among the metal oxides are included such materials as silica, alumina, zirconia, thoria, and combinations thereof. Silica and alumina are preferred materials of this invention, and among the aluminas gamma-alumina is especially preferred. In some applications glass or ceramic materials may be desirable. The one characteristic common to all the core supports of this invention is their ability to be silylated with appropriate organosilanes.

The spacer molecules of this invention are organosilanes. Their function is to firmly bind the chiral molecules to the core support while holding such molecules sufficiently distant from the surface of the core support so as to permit the chiral molecule to approximate the physical and chemical properties it exhibits under homogeneous conditions. Such organosilanes are derived from materials, whose formula may be given as UVW-Si(CH$_2$)$_n$B, which are characterized as having the ability to react with surface hydroxyl groups of the core support to form oxygen-silicon bond(s), i.e., all have the ability to silylate the core supports.

The value of n may be from 1 to about 10, with n equal to 3 being a preferred material. This chain of mediating carbon atoms performs the spacer function. B is a functional group, such as halogen, amino, or mercapto, which subsequently reacts with the chiral acid leading to a covalent bond. For example, when B is a halogen, it may react with an amino group of amino acids forming a carbon-nitrogen bond. When B is an amino group, it may react with a carboxyl or an activated carboxyl group, for example, an anhydride or acid halide, to form an amide linkage. In the invention described herein B is an amino group.

The groups U, V, and W, are selected from the group consisting of alkoxy groups containing from 1 to about 10 carbon atoms, and alkyl groups containing from 1 to about 10 carbon atoms. It is required that at least one of such groups is not alkyl, and it is preferable that any alkyl group contain no more than about three carbons atoms. Where U, V, or W is an alkoxy group, it reacts with the surface hydroxyl groups of the core support resulting in the spacer molecule becoming firmly attached to the surface. Thus the number of linkages between the silicon atoms of the organosilane and the oxygen atoms of the core support may be equal to the number of alkoxy groups of the organosilane, although it may be that no more than two such linkages occur. Where U, V, and W are each alkoxy groups, the maximum attachment to the surface of the core support results, which is highly desirable.

Examples of precursors of spacer molecules which may be utilized in this invention include 3-aminopropyl-trimethoxysilane, 3-aminopropyl-triethoxysilane, 3-aminopropyl-tripropoxysilane, 3-aminopropyl-tributoxysilane, 3-aminopropyl-tripentoxysilane, 3-aminopropyl-dimethoxyethoxysilane, 3-aminopropyl-diethoxymethoxysilane, 3-aminopropyl-methoxyethoxypropoxysilane, 3-aminopropyldimethoxymethylsilane, 3-aminopropyl-dimethoxyethylsilane, 3-aminopropyl-dimethoxypropylsilane, 3-aminopropyl-methoxyethoxypropylsilane, 4-aminobutyltrimethoxysilane, 5-aminopentyl-trimethoxysilane, 6-aminohexyl-trimethoxysilane, 10-aminodecyl-trimethoxysilane, etc.

The chiral molecules of this invention comprise the class of amino acids and their derivatives, and naturally occurring amino acids and their derivatives are especially preferred. Examples of such amino acids include alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, and valine. Such amino acids are immobilized, or bound, by reaction of the amino group at the terminus of the alkylsilyl moiety with a carboxyl, or activated carboxyl, group of the amino acid or derivatives thereof, forming a carbon-nitrogen bond via an amide linkage. That is, bonding of the amino acid occurs by amidation of the carboxyl group by the aminoalkylsilyl moiety.

Derivatives of amino acids often may be employed advantageously. The nature of the derivative frequently will depend upon the nature of the amino acid immobilized. Where the bound chiral amino acid has a free carboxyl group, as in aspartic and glutamic acids, one general class of derivatives may be those of the carboxyl group, for example, esters, amides, alkyl, aryl, and aralkyl amides, urethanes, thioesters, etc. Examples of suitable esters include methyl, ethyl, propyl, butyl, pentyl, hexyl, heptyl, octyl, allyl, phenyl, benzyl, naphthyl, 2-phenylethyl esters, etc.

When the bound amino acid has a free amino group, as will be the case for all amino acids of this invention, another class of derivatives is that of such an amino group. Among the more desirable derivatives are amides, alkyl, aryl, and aralkyl substituted amides, and certain aryl substituted amines. Examples of suitable amides include those formed from acids such as acetic, propionic, butyric, caproic, capric, chloroacetic acid, fluoroacetic, bromoacetic, benzylic, phenylacetic, acrylic, phenylacrylic acids, etc. Among the aryl substituted amines which are desirable are included benzyl, nuclear substituted benzyl, 9-anthryl, and nuclear substituted 9-anthryl amines.

Several of the amino acids of this invention have a free hydroxyl available. Therefore another class of derivatives is that of the hydroxyl group, for example, esters and ethers. Examples of suitable esters are those from acids described above as suitable in forming amides of the free amino group, while examples of ethers include simple alkyl ethers, such as methyl, ethyl, propyl, butyl, pentyl, hexyl, allyl, etc., and aryl ethers; such as phenyl, naphthyl, anthryl, and aralkyl ethers, such as benzyl, xylyl, chlorobenzyl, etc.

The most desirable derivatives of this invention are pi-acids and pi-bases. Pi-acids are compounds characterized as good electron acceptors capable of weak bonding interactions with electron donors to form entities commonly known as pi-complexes. Reciprocally, pi-bases are good electron donors capable of weak bonding interactions with electron acceptors to form pi-complexes.

The pi-acids and -bases of this invention are structures incorporating one or more aromatic rings, such as benzene, naphthalene, anthracene, fluorene, indene, chrysene, phenanthrene, and the like. Although an unsubstituted aromatic ring may suffice to act as a suitable pi-acid or -base, preferred pi-acids are those where the aromatic ring bears at least one electronegative moiety, and preferred pi-bases are those where the aromatic ring bears at least one electropositive moiety. Still more preferred pi-acids and -bases are those where the aromatic ring bears a plurality of electronegative or electropositive moieties, respectively. Electronegative moieties may be selected from the group consisting of nitro, bromo, chloro, fluoro, trifluoromethyl, trialkylammonium, cyano, sulfonyl, and any combination thereof. Electropositive moieties may be selected from the group consisting of alkyl, amino, alkylamino, dialkylamino, alkoxy, hydroxy, carbonyl, and any combination thereof.

To exemplify the aforementioned derivatives of this invention acting as pi-acids or pi-bases, the following are cited solely for purposes of illustration: esters of nitrophenol, polynitrobenzyl alcohol, polytrifluoromethylphenol, cyanofluoroanthracene methanol, fluorochloronaphthol, cresol, anisole, aminophenol, polydimethylamino phenol, polyalkylnaphthol, etc.; amides of chloro, bromo, and fluorobenzoic acid, polyfluorobenzoic acid, trifluoromethylnaphthoic acid, polynitrophenylacetic acid, polycyanoanthracene carboxylic acid, hydroxybenzoic acid, polydialkylaminobenzoic acid, acetylbenzoic acid, polyalkylnaphthoic acid, etc.; N-aryl and aralkylamines wherein the aryl group is a polyfluorophenyl, nitrophenyl, fluoronitrophenyl, trialkylammoniumphenyl, polytrifluoromethylnaphtyl, chlorocyanoanthracenyl, dialkylaminophenyl, alkoxynaphthyl, polyalkylanthracenyl, etc.; and similarly constituted urethanes, thioesters, ethers, etc.

From the foregoing description of this invention it is to be understood that the compositions described herein may be represented, at least in part, by the structure $XYZSi(CH_2)_n$-N-A. At least one member of the group X,Y,Z is an oxygen atom associated with the surface of the core support, not otherwise shown here, with the remaining members being alkyl or alkoxyl containing from 1 to about 10 carbon atoms. In a preferred mode each of two or more members of the group X,Y,Z is an oxygen atom of said surface of said support. The chain of mediating atoms, $(CH_2)_n$, performs the spacer function, with n an integer from about 1 to about 10, and n equaling 3 being a preferred mode. The structure $XYZ$-$Si(CH_2)_n$-may be termed the spacer molecule. The chain of mediating atoms terminates in a nitrogen atom, N, which is part of the carboxamide moiety, NCO, the carboxyl portion of which originates from a chiral amino acid whose remaining portion is here designated as A. Thus, the chiral amino acid is covalently bonded to a terminus of the spacer molecule.

The compositions of this invention may be prepared by any suitable method. One such method commonly employed utilizes a preliminary drying of the inorganic oxide, generally under vacuum and at temperatures up to about 200° F., for times up to about 24 hours, the particular temperature and time depending upon the nature of the oxide. The dried inorganic oxide is then treated with a silylating agent, such as 3-aminopropyltriethoxysilane, in a solvent under an inert atmosphere. A solvent system comprised of an aromatic solvent, such as toluene, and an organic base, such as pyridine, frequently is advantageous. The mixture may be stirred at temperatures from about 50° to about 100° C. for a time sufficient for silylation, generally from 5 to 50 hours. The resulting silylated inorganic support is then separated, as by filtration, and washed successively with organic solvents, such as alcohols, ketones, and hydrocarbons, to remove residual solvents while maintaining the silylated material in a more or less anhydrous condition. Silane loadings of from about 0.1 to about 10 millimoles per gram of inorganic oxide may be obtained, although typically loadings of about 1 millimole per gram may be observed.

The coupling, or bonding, of an amino acid to the silylated support by amidation of a carboxyl group may be done in any suitable way known in the art. Quite commonly the chiral amino acid, or a derivative thereof, is contacted with the silylated inorganic oxide in the presence of a coupling reagent, such as N-ethoxycarbonyl-2-ethoxy-1,2-dihydroquinoline (EEDQ), for a time from about 3 to about 30 hours, at a temperature near ambient. Solid is separated, as by filtration, then washed with organic solvents to remove adhering but unbound organic material.

The examples cited below serve only to illustrate this invention. They are not to be construed in any way as a limitation thereof.

EXAMPLE 1

Silica gel (4.0 g of 10 micron Partisil from Whatman, Inc.) was dried at 1 mm. Hg. at 150° C. for six hours. Dry nitrogen was admitted to the cooled silica gel, and about 7 ml. of 3-aminopropyltriethoxysilane dissolved in 20 ml. of a 1:1 solution of dried pyridine and toluene were quickly added. The mixture was maintained at 80° C. for 48 hours with occasional stirring in an inert atmosphere, such as nitrogen. The solid was removed by filtration and washed successively with methanol, acetone, diethyl ether, and pentane. The silylated silica gel then was air dried, and finally vacuum dried to remove residual solvents.

L-(+)-histidine (2.86 g, 0.0136 mol), 3,5-dinitrobenzoyl chloride (3.31 g, 0.0144 mol) and 50 ml. of dichloromethane were stirred at room temperature, protected from moisture, for 96 hours. The solvent was evaporated at reduced pressure, and the solid residue was contacted with 5% aqueous sodium bicarbonate. Solid was removed by filtration, and the filtrate was continuously extracted for 12 hours with diethyl ether. The solid obtained from the ether extract was combined with the solid collected by filtration to afford 2.86 g, 60%, of L-(+)-N-(3,5-dinitrobenzoyl)histidine (DNB-HIS), melting point 182°–184° C.

The DNB-HIS was added to a slurry of 3.0 g of 3-aminopropylsilica gel, prepared as above, and 65 ml. of dry tetrahydrofuran. To this was added 2.0 g (0.00809 mol) of N-ethoxycarbonyl-2-ethoxy-1,2-dihydroquinoline (EEDQ). After 25 hours at room temperature under a nitrogen blanket with occassional stirring, the gel was separated by filtration and washed with methanol, acetone, and diethyl ether to afford 3.28 g of light tan solid. Analysis indicated 0.40 mmol of chiral material was immobilized.

EXAMPLE 2

L-(−)-N-(3,5-dinitrobenzoyl)-phenylalanine (DNB-PALA) was prepared in a manner identical to the preparation of DNB-HIS using 3.0 g (0.0182 mol) of phenylalanine, 4.41 g (0.0191 mol) of 3,5-dinitrobenzoyl chloride, and 70 ml. of dichloromethane. The product was obtained in 59% yield as a tan colored powder.

DNB-PALA was coupled to silylated silica gel as was described in example 1 using 3.36 g (0.00935 mol) of DNB-PALA, 2.51 g (0.00984 mol) of EEDQ, 3.36 g of 3-aminopropylsilica gel, and 70 ml. of tetrahydrofuran. A total of 4.95 g of immobilized chiral amino acid ester was obtained of a light lavender color.

EXAMPLE 3

L-(−)-phenylalanine may be treated with a slight excess of alpha-bromo-9-methylanthracene in dichloromethane and enough triethylamine to scavenge the formed hydrogen bromide. After 4 hours, the solvent and excess amine may be evaporated under reduced pressure. The residue may be dissolved in dichloromethane which then may be extracted with water. The dried organic layer may be concentrated to yield L-(−)-N-(alpha-(9anthryl) methyl) phenylalanine, which may be coupled to silylated silica gel using EEDQ and 5-aminopentylsilyl silica gel as described in Example 1.

What is claimed is:

1. A composition for resolution of racemic mixtures comprising:
   (a) a core support selected from the group consisting of silica and alumina;
   (b) a spacer molecule, one terminus of which is bonded to at least one oxygen atom of the core support via a silicon atom;
   (c) a chiral amino acid or derivative thereof covalently bonded to the remaining terminus of the spacer molecule via amidation of a carboxyl group so as to retain its chirality.

2. The composition of claim 1 wherein the alumina is gamma alumina.

3. The composition of claim 1 wherein the spacer molecule is an organosilane of the formula XYZ-Si(CH$_2$)$_n$—, where at least one member of the group, X, Y, Z is an oxygen atom associated with a surface of the organic oxide, and the remaining members are selected from the group consisting of alkyl and alkoxy containing from about 1 to about 10 carbon atoms, n is an integer from about 1 to 10, and the remaining terminus of said spacer molecule is covalently bonded via a carboxamide group to said chiral amino acid.

4. The composition of claim 3 wherein each of at least two members of the group X, Y, Z is an oxygen atom associated with a surface of the inorganic oxide.

5. The composition of claim 3 wherein n is equal to 3.

6. The composition of claim 1 wherein the chiral amino acid and derivatives thereof is a naturally occurring amino acid and derivatives thereof.

7. The composition of claim 6 wherein the derivatives of said chiral amino acid are selected from the group consisting of ethers, esters, amides, and N-arylamines.

8. The composition of claim 7 wherein the derivatives are pi-acids.

9. The composition of claim 7 wherein the derivatives are pi-bases.

* * * * *